United States Patent [19]

Romanski et al.

[11] 3,937,797

[45] Feb. 10, 1976

[54] PRODUCTION OF HARD TITANIA

[75] Inventors: Andrzej Antoni Florian Romanski; Derek John Brookes, both of Sheffield; Anthony Smith, Rotherham; Harry Markham, Sheffield, all of England

[73] Assignee: British Steel Corporation (Chemicals) Limited, Great Britain

[22] Filed: June 3, 1974

[21] Appl. No.: 475,910

[30] Foreign Application Priority Data

June 4, 1973 United Kingdom............... 26484/73

[52] U.S. Cl.............. 423/610; 23/293 R; 23/293 A; 252/461
[51] Int. Cl.².................... B01J 9/02; B01J 35/02; C01G 23/04; C22B 34/00
[58] Field of Search.............. 23/293 A, 293 R, 305; 423/610; 106/300; 252/461

[56] References Cited
UNITED STATES PATENTS

| | | | |
|---|---|---|---|
| 1,850,154 | 3/1932 | Raspe et al. | 23/293 A UX |
| 2,721,787 | 10/1955 | Hettrick | 23/293 R X |
| 2,771,345 | 11/1956 | Tanner, Jr. | 423/610 |
| 2,968,537 | 1/1961 | Nixon | 23/293 R |
| 3,632,527 | 1/1972 | Alpert et al. | 423/610 UX |
| 3,719,748 | 3/1973 | Manfroy et al. | 423/610 X |

*Primary Examiner*—Joseph Scovronek
*Assistant Examiner*—Michael S. Marcus
*Attorney, Agent, or Firm*—Cushman, Darby & Cushman

[57] ABSTRACT

Method of hardening powdered titania (titanium dioxide) so as to make it attrition-resistant and to enhance its properties as a catalyst carrier. The method involves thoroughly dispersing powdered titanium dioxide in water, removing the excess water, drying and then calcining the product at a temperature between 650°C and 900°C. Preferably a large excess of water is used, at least 37% to effect dispersion; and dispersion may be aided by use of a surfactant, a water soluble organic compound or a highly polar inorganic compound. The excess water may be removed by filtration or the use of flocculants.

The resultant powdered material is particularly useful as a carrier for oxidising ortho-xylene to phthalic anhydride.

7 Claims, No Drawings

PRODUCTION OF HARD TITANIA

Catalysts for use in fluid bed processes such as the oxidation of o-xylene to phthalic anhydride must have good fluidizing characteristics and have a high degree of resistance to attrition. Fluidizing characteristics are related to particle size and size distribution. If the catalyst has been manufactured by impregnating or coating with active components a catalyst carrier which is intrinsically weak, large quantities of fine particles will be produced early in its life. These will impair fluidization, initiating the phenomenon known as chanelling whereby unduly high gas velocities exist in certain regions of the bed cross section and perhaps even causing the formation of 'dead-spots' on some areas of the distribution plate. Under these circumstances, in contrast to a perfect fluid bed, reaction conditions vary widely throughout the bed making optimization of yield impossible. In addition, excessive quantities of finely divided catalyst are present in the disperse phase of the reactor, placing an additional load on catalyst filters. These will either have to operate at excessive differential pressures or provision be made in reactor design to allow for additional filter surface area. In addition, the presence of greater quantities of fine catalyst will increase the risk of uncontrolled reactions occurring in this region and consequently of fire.

The use of titania as a carrier for oxidation reactions carried out in fixed beds (particularly when oxidizing o-xylene to phthalic anhydride) is well known to those experienced in the art but its use has not so far been found practical in fluid beds because of the poor mechanical strength of titania particles available. The object of this invention is to provide a method of hardening powdered titanium dioxide (anatase or rutile) for use as a catalyst carrier.

According to the invention, a method of hardening powdered titania comprises thoroughly dispersing the powder in water, removing the excess water, drying and calcining. Dispersion is preferably carried out using a large excess of water. If the quantity used is not in excess of the minimum needed just to wet the titania and achieve complete dispersion, the final product may be of variable quality.

Dispersion may be aided by using additions of agents such as surfactants, certain water soluble organic compounds and highly polar inorganic compounds.

For practical purposes, the excess water should first be removed to yield a paste which can be dried easily. This may be achieved by filtration, the incorporation of flocculants in the original 'mix' used or other suitable methods.

The paste must then be dried prior to calcination. The most suitable drying conditions are dependant on the moisture content of the paste and the area of surface exposed to the drying conditions.

If this is not done, the rapid evolution of water vapour will cause disintegration of the structure of the base and may result in the formation of pores thus lowering its strength. If the drying temperature is too low, the time required may be excessive.

Careful control of the calcination stage is important, because this affects the hardness and surface area of the final product. Also, in the case of anatase, if too high a temprature is used isomerization to rutile will take place which will reduce the selectivity of catalysts made from it for certain reactions.

A suitable product is obtained if the dried anatase paste is calcinated at temperatures between 700° – 900°C, preferably between 800° – 850°C. If rutile is employed the lower limit can be 650°C.

We have found, that if during the initial dispersion procedure the quantity of water added is increased, mixing is made easier. For example, the addition of 37 parts of water to 63 parts of British Titan Products AHR grade anatase enables satisfactory mixing to be carried out, even in large batches.

In the presence of this large excess of water, the powdered anatase is dispersed very readily. In order to process this material further, it is necessary to remove the excess water present. Failure to do so will make the drying procedure very difficult to carry out. The excess water may be removed by means of suitable, commerically available equipment e.g. rotary drum vacuum filtration. Alternatively, the wetting procedure may be modified to reduce the quantity of water required.

The use of suitable additives in this operation has been found both to aid mixing and reduce the total volume of water needed. The product obtained then has a soft cheese like consistency, can be handled more conveniently and requires less drying before calcination.

Examples of commercial ionic surfactants which can be used as additives are:— Bitran 02 — a cationic surfactant which is a long chain amine derivative; Arquad S/50 — a cationic quarternary ammonium salt, and the sodium sulphonate-based Teepol.

Use of a surfactant eases mixing although usually with a resultant loss of hardness of the final product but not necessarily to such a degree that it cannot be used successfully as a catalyst carrier.

Examples of water soluble organic compounds which can be used include acetone, acetic acid, methyl alcohol, ethyl alcohol, propanol, n butanol and 2 butanol. The improved ease of mixing obtained by using these water soluble organic compounds is also usually accompanied by some reduction in the hardness of the final product but not necessarily to such a degree that it cannot be used successfully as a catalyst carrier.

Examples of highly polar inorganic compounds which can be used include hydrochloric acid, nitric acid, phosphoric acid, caustic soda and sodium nitrate.

Another method of producing a product suitable for drying is by the use of a flocculant as an additive in the wetting stage. Zimmite, a flocculating agent of the modified polyacrylamide type has been found to be particularly suitable. The flocculating agent may conveniently be used by adding in the aqueous phase to the titania which has been dispersed in a large excess of water. The mixture is then stirred until the suspension coagulates. After settling, the supernatant liquid is syphoned off leaving a wet pulp which can be partially dewatered by pressing.

The mechanical strength of the catalyst carrier normally obtained using this method is comparable to that using water alone.

EXAMPLE 1

Anatase and Water Alone 1 kg of commercial pigment grade anatase e.g. British Titan Products Ltd. grade AHR was dispersed in 600 g of water. The excess was removed by filtration, yielding a paste containing 25% by wt. of water. This was then placed in a tray in a one inch deep layer and then dried in an oven at 100°C for 4 hours. The dried material was placed directly into a muffle at 800°C and calcined for two hours giving a product with a friability index of 74.

EXAMPLE 2

Addition of a Surfactant 1 kg of commercial pigment grade anatase e.g. British Titan Products Ltd. grade AHR and 440 mls of an aqueous solution of 0.75. Bitran 02 a cationic surfactant were mixed together with stirring, and left to dry in a 1 inch layer for 15 hours at ambient temperature before calcination as in Example 1 giving a product with a friability index of 65.

EXAMPLE 3

The Use of Flocculant to Remove Excess Water 1 kg of commercial pigment grade anatase e.g. British Titan Products Ltd. grade AHR was dispersed in 2 liters of water. To this 1.17 liters of 0.2% Zimmite a modified polyacrylamide in water was added with stirring. Two hours was then allowed for the anatase to coagulate and settle. The supernatent liquid was syphoned off, and a wet doughlike material (ca. 38% water content) left which was further dewatered by pressing. This was placed in a drying tray in a 1 inch deep layer and heated at 120°C for 4 hours.

The material obtained by this method can also be dried at high temperatures (150°C) without impairing the properties of the final product. The dried material is calcined as in Example 1 giving a product with a friability index of 75.

EXAMPLE 4

1 kg of British titan Products Ltd. grade RSM rutile was dispersed in 600 g of water. The excess water was removed by filtration yielding a paste containing 25% by wt. of water. This was then placed in a tray in a one inch deep layer and then dried in an oven at 100°C for 4 hours. The dried material was placed directly into a muffle at 800°C and calcined for two hours giving a product with a friability index of 85.

EXAMPLE 5

1 kg of commercial pigment grade anatase, e.g. British Titan Products Ltd. grade AHR anatase, and 550 mls of a solution of 0.1% v/v conc. nitric acid in water were mixed together with stirring. A smooth, homogeneous paste was readily obtained which was then dried in a 1 inch thick layer for 10 hours at 70°–80°C before calcination (as in example 1) giving a product with a friability index of 71.5.

EXAMPLE 6

1 kg of commercial pigment grade anatase. e.g. British Titan Products Ltd. grade AHR anatase, and 720 mls of a solution of 1% w/v sodium hydroxide in water were mixed together with stirring. A smooth, homogeneous paste was readily obtained which was then dried in a 1 inch thick layer for 15 hours at 80°C before calcination (as in example 1) giving a product with a friability index of 76.2.

EXAMPLE 7

1 kg of commercial pigment grade anatase e.g. British Titan Products Ltd. grade AHR anatase, and 700 mls of a solution of 1. w/v sodium nitrate in water were mixed together with stirring. A smooth homogeneous paste was readily obtained which was then dried in a 1 inch thick layer for 15 hours at 80°C before calcination (as in example 1) giving a product with a friability index of 75.2.

EXAMPLE 8

1 kg of commercial pigment grade anatase, e.g. British Titan Products Ltd. grade AHR anatase, and 520 mls of a solution of 10% v/v butan 2-ol in water were mixed together with stirring. A smooth, homogeneous paste was readily obtained which was then dried in a 1 inch thick layer for 10 hours at 70°–80°C before calcination (as in example 1) giving a product with a friability index of 68.9.

TESTING

The resistance of anatase samples to mechanical disintegration is compared by the modified ball-mill test, which was originally developed for testing the microstrength of coke (H. E. Blyden, W. Noble, H. L. Riley, J. Iron & Steel Institute, 47P. 1937. 75P 1939).

In this method, which differs from the original only in experimental details resulting from the different strengths of two materials, 1 gm of base of 14–16 B.S.S. size grading is placed in a ¾ inch dia. 8½ long steel tube together with three ¼ inch dia. steel balls and rotated for 370 revolutions at 25 R.P.M.

The friability index is defined as the percentage of base which after testing is retained on a 25 B.S sieve. The greater the strength of the material the higher the friability index.

We claim:

1. A method of hardening powdered titania comprising thoroughly dispersing a composition consisting essentially of commercial pigment grade anatase or rutile in a large excess of water, removing excess water to form a paste of said titania and water, drying said paste and then calcining the titania at a temperature of 650°C to 900°C.

2. A method according to claim 1 and in which the removal of the excess water is achieved by filtration.

3. A method according to claim 1 and in which the powdered titania is anatase.

4. A method according to claim 3 and in which the anatase is British Titan Products AHR grade anatase.

5. A method according to claim 1 and in which the calcination temperature is between 800°C and 850°C.

6. A method according to claim 1 in which the amount of water, as a percentage of the water plus titanium dioxide, is at least 37%.

7. A carrier for oxidising ortho-xylene to phthalic anhydride which consists of titania prepared in accordance with the method of claim 1.

* * * * *